(12) United States Patent
Kulovesi et al.

(10) Patent No.: US 12,029,483 B2
(45) Date of Patent: Jul. 9, 2024

(54) SYSTEM AND METHOD FOR FINDING AN AREA OF AN EYE FROM A FACIAL IMAGE

(71) Applicant: Revieve Oy, Helsinki (FI)

(72) Inventors: Jakke Kulovesi, Helsinki (FI); Samuli Siivinen, Valencia (ES)

(73) Assignee: Revieve Oy, Helsinki (FI)

( * ) Notice: Subject to any disclaimer, the term of this patent is extended or adjusted under 35 U.S.C. 154(b) by 731 days.

(21) Appl. No.: 17/004,751

(22) Filed: Aug. 27, 2020

(65) Prior Publication Data

US 2022/0061659 A1    Mar. 3, 2022

(51) Int. Cl.
| | | |
|---|---|---|
| *A61B 3/11* | (2006.01) | |
| *G06V 10/56* | (2022.01) | |
| *G06V 40/16* | (2022.01) | |
| *G06V 40/18* | (2022.01) | |
| *A61B 3/10* | (2006.01) | |

(52) U.S. Cl.
CPC ............ *A61B 3/112* (2013.01); *A61B 3/1025* (2013.01); *G06V 10/56* (2022.01); *G06V 40/165* (2022.01); *G06V 40/171* (2022.01); *G06V 40/193* (2022.01)

(58) Field of Classification Search
CPC ...... A61B 3/112; A61B 3/1025; G06V 10/56; G06V 40/171; G06V 40/165; G06V 40/193
USPC .......................................................... 351/206
See application file for complete search history.

(56) References Cited

U.S. PATENT DOCUMENTS

| | | | | |
|---|---|---|---|---|
| 2013/0076932 | A1* | 3/2013 | Chhibber | G06V 40/162 |
| | | | | 348/222.1 |
| 2015/0339512 | A1* | 11/2015 | Son | H04N 23/71 |
| | | | | 348/78 |
| 2016/0085302 | A1* | 3/2016 | Publicover | G02B 27/0172 |
| | | | | 345/633 |
| 2016/0210503 | A1* | 7/2016 | Yin | G06T 7/73 |
| 2017/0352135 | A1* | 12/2017 | Florea | G06T 5/00 |

OTHER PUBLICATIONS

European Patent Office, Extended European Search Report, Application No. 21185196.9, dated Dec. 22, 2021, 9 pages.

(Continued)

*Primary Examiner* — Sharrief I Broome
(74) *Attorney, Agent, or Firm* — Ziegler IP Law Group LLC.

(57) ABSTRACT

An eye segmentation system for determining a center point of an eye, a radius of an iris of the eye, and an area of interest from a white area (sclera) of the eye. The system includes at least one input interface that receives a facial image of a user, wherein the facial image is captured using an image capturing device and a data processing arrangement that receives the facial image of the user as input data and processes the facial image to segment an eye region of the facial image. The system determines an eye that is suitable for segmentation from a left eye and a right eye using at least one quality metric, determines a center point of the eye using at least one directional filter, determines, using the at least one directional filter, a radius of an iris of the eye from the center point of the eye.

21 Claims, 7 Drawing Sheets

(56) References Cited

OTHER PUBLICATIONS

Feng et al., "Accurate iris center localization method using facial landmark, snakuscule, circle fitting and binary connected component" Multimedia Tools and Applications, vol. 77, No. 19, pp. 25333-25353, XP036580506, ISSN: 1380-7501, DOI: 10.1007/S11042-018-5787-X, Feb. 23, 2018, 21 pages.

Nigam et al., "Ocular biometrics: A survey of modalities and fusion approaches", Information Fusion, vol. 26, pp. 1-35, XP029235976, ISSN: 1566-2535, DOI: 10.1016/J.INFFUS.2015.03.005, Apr. 15, 2015, 35 pages.

Zhi et al., "A New Human Identification Method: Sclera Recognition", IEEE Transactions on Systems, Man, and Cybernetics—Part A: Systems and Humans, vol. 42, No. 3, pp. 571-583, XP055082577, ISSN: 1083-4427, DOI: 10.1109/TSMCA.2011.2170416, May 1, 2012, 13 pages.

\* cited by examiner

SYSTEM AND METHOD FOR FINDING AN AREA OF AN EYE FROM A FACIAL IMAGE

TECHNICAL FIELD

The present disclosure relates generally to a system and method of facial image processing, more specifically to eye color and skin color detection.

BACKGROUND

"Eye segmentation" is a process of segmenting an image of an eye, for example derived from a portion of a captured facial image. Such image segmentation partitions a digital image of an eye into multiple segments known as "image objects". A goal of image segmentation is to transform a representation of a given image into a corresponding transformed version of the given image, wherein the transformed image is more meaningful and easier to analyze. The image segmentation is typically used to locate objects and boundaries, for example, lines, curves, etc. in images.

Segmenting a portion of an image of a face, wherein the portion corresponds to an eye, is useful for many applications. For example, there are many known types of executable software applications that are available for making recommendations for cosmetic products, such as cosmetic makeups. One such executable software application enables a user to capture an image (e.g. photo) of the user's face, for example in a "selfie mode" of image capture, whereafter the image is used to test mutually different types of makeups such as lipstick, mascara, blush, eye shadow, foundation, etc. that are virtually superimposed on top of the image.

Generally, the makeups have mutually different colors and their final effect on appearance is mainly dependent on a skin tone, a skin color, and a skin type of a given user. After using the executable software application to test different options for the cosmetic products, the given user is then potentially motivated to buy a cosmetic product that suits the given user. Existing executable software applications that detect eye color for makeup do not detect eye locations within an image to a sufficient accuracy, wherein such an accuracy is important to achieve when making recommendations on cosmetic products; the cosmetic products are used, for example, to modify a color of a skin of the user.

Known pattern recognition algorithms are available for detecting an eye or other part of an image of a face of the user. However, the pattern recognition algorithms are found to be unreliable and problematic when the user wears eyeglasses in the image, wherein the user's eyes are partly closed in the image, or the image is of low quality and captured in poor illumination conditions. Furthermore, random stochastic noise, for example image sensor noise, physical obstructions partially covering the eyes, eyeglasses, makeup, poor illumination conditions, etc. present in the image potentially creates artificial edges in the image, which potentially cause the pattern recognition algorithms to function erratically. Evenly distributed noise potentially causes the pattern recognition algorithms to detect "false candidates" when seeking to identify an eye in a facial image. Similarly, existing image recognition and image analysis algorithms are inaccurate in finding a position of an eye in a facial image, when the image includes imperfect data.

Therefore, there is a need to address aforementioned technical drawbacks in existing technologies in segmenting from a facial image a portion of the image corresponding to an eye; these drawbacks are especially encountered when a user wears eyeglasses, wherein the user's eyes are partly closed or the image is of low quality and captured in poor illumination conditions.

SUMMARY

The present disclosure seeks to provide an improved system and method for finding at least one area of interest of a graphical representation of an eye from a facial image, even when the user is wearing eyeglasses or the user's eye is partly closed in the facial image, or the facial image of the user is of a low quality. The present disclosure further seeks to reduce an effect of artificial edges present in the facial image due to random noise, thereby improving an accuracy of detection of the eye and its parts. The present disclosure seeks to provide a system and a method to function more reliably when processing very low-quality images and when determining a color of an eye in an efficient way to provide recommendations on one or more cosmetic products to the user.

According to a first aspect, there is provided a method for finding at least one area of interest of a graphical representation of an eye from a facial image, the method comprising executing instructions by implementing steps of:
  receiving the facial image of a user as an input data;
  detecting a first area from the facial image, wherein the first area comprises the graphical representation of the eye of the user and the first area is surrounded by an edge;
  determining a center point of an iris and a radius of the iris of the graphical representation of the eye by scanning the first area using at least one directional filter.

The advantage of the embodiments according to the present disclosure in that the at least one direction filter enables the center point of the iris and the radius of the iris to be identified more reliably, even when there is stochastic noise present within the facial image.

According to a second aspect, there is provided a system for finding at least one area of interest of a graphical representation of an eye from a facial image, the system comprising a memory configured to store instructions; a data processing arrangement that is configured to execute the instructions to
  receive the facial image of a user as an input data;
  detect a first area from the facial image, wherein the first area comprises the graphical representation of the eye of the user and the first area is surrounded by an edge;
  determine a center point of an iris and a radius of the iris of the graphical representation of the eye by scanning the first area using at least one directional filter.

According to a third aspect, there is provided a computer program comprising computer readable instructions adapted to perform the method of the first aspect.

It will be appreciated that the aforesaid method of the first aspect is not merely a segment "for finding at least one area of interest of a graphical representation of an eye from a facial image", but has a technical effect in that the method receives stochastically noisy data representing a facial image of a user, wherein the stochastically noisy data is obtained from an image capturing device, and automatically processes the facial image to segment a portion of the image corresponding to an eye using at least one directional filter. The method of automatically segmenting the portion of the image corresponding to the eye involves using at least one of: (i) the at least one directional filter; and (ii) using the at least one directional filter to address (for example, to solve) the technical problem of segmenting a portion of a facial image corresponding to an eye by automatically determining whether a left eye or a right eye in the facial image is suitable for being used, wherein such a determination utilizes at least one quality metric for determining the center point of the eye and a radius of an iris of the eye.

Furthermore, compensating at least one element of the eye segmentation system that automatically segments the image of the eye optionally causes a hardware reconfiguration of the eye segmentation system, for example at least one of: (i) selectively switches in additional processor capacity, (ii) selectively switches in more data memory capacity, (iii) selectively switches in mutually different types of graphic processor chip, wherein a status of the hardware reconfiguration is regarded as being technical in nature and providing a technical effect, for example coping with the aforementioned stochastic noise present in the captured image.

Embodiments of the present disclosure substantially eliminate, or at least partially address, the aforementioned technical drawbacks in segmenting from the facial image a portion of the facial image corresponding to the eye, especially when the user is wearing eyeglasses or the user's eye is partly closed in the facial image or the facial image is of low quality and captured in poor illumination conditions. Additional aspects, advantages, features, and objects of the present disclosure are made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers. Embodiments of the present disclosure will now be described, by way of example only, with reference to the following diagrams wherein.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

According to a first aspect, there is provided a method for finding at least one area of interest of a graphical representation of an eye from a facial image, the method comprising executing instructions by implementing steps of:
receiving the facial image of a user as an input data;
detecting a first area from the facial image, wherein the first area comprises the graphical representation of the eye of the user and the first area is surrounded by an edge;
determining a center point of an iris and a radius of the iris of the graphical representation of the eye by scanning the first area using at least one directional filter.

The method uses a segmentation process by segmenting from the captured facial image of the user a portion of the facial image corresponding to the user's eye, even when the user is wearing eyeglasses or the user's eye is partly closed in the facial image, or the facial image of the user is of a low quality. Moreover, the method reduces an effect of artificial edges created on the facial image due to random noise by using directional filtering, thereby improving a reliability and accuracy of detection of the portion of the facial image corresponding to the eye and its parts. The method is able to function reliably when presented with very low-quality images and is able to determine the color of the eye in a more accurate and efficient way to provide recommendations in respect of one or more cosmetic products to the user.

Optionally, the method comprises determining a sclera area of the graphical representation of the eye to be an area between the edge and a circle, the circle having the determined center point of the iris and the radius of the iris.

Optionally, the method further comprises determining a pupil area of the graphical representation of the eye by implementing a contrast analysis and using the center point of the iris and the radius of the iris.

Optionally, the method further comprises determining an iris area to be an area between the circle having the center point and the radius of the iris and the pupil area.

Optionally, the method further comprises determining the edge of the first area by identifying at least one eye point around the graphical representation of the eye using an image processing technique.

Optionally, when using the method, determining the center point of the iris comprises scanning, using the at least one directional filter, x values of the first area in a first direction and scanning, using the at least one directional filter, in a second direction to index y values of the first area. More optionally, when using the method, determining the center point of the iris further comprises identifying a point that is correlating to a center of the first area based on the scanning the first area using the at least one directional filter in the first direction and the second direction.

Optionally, when using the method, determining the radius of the iris comprises
   determining a first radius of the iris by applying a first directional filter over the first area through a first path, wherein applying the first directional filter over the first area through the first path comprises (i) scanning, using the first directional filter, x values of the first area in a first direction, and (ii) scanning, using the first directional filter, the first area in a second direction to index y values of the first area;
   determining a second radius of the iris by applying a second directional filter over the first area through the first path, wherein applying the second directional filter over the first area through the first path comprises (i) scanning, using the second directional filter, x values of the first area in the first direction, and (ii) scanning, using the second directional filter, the first area in the second direction to index y values of the first area; and
   identifying the radius of the iris, from the first radius or the second radius of the iris, which is correlated with the center point of the iris.

Optionally, the method comprises determining a radius of the pupil area by
   performing a radial scan, using the at least one directional filter, over the graphical representation of the eye;
   identifying a brightness change in the first area to determine a border of the pupil area; and
   combining the identified brightness change of the graphical representation of the eye and probability distribution of the radius of the pupil area.

Optionally, when using the method, determining the sclera area comprises
   calculating a first sclera criteria and a second sclera criteria for the graphical representation of the eye;
   combining the first sclera criteria and the second sclera criteria with the first area of the graphical representation of the eye to calculate a threshold value; and
   applying the threshold value on the graphical representation of the eye to determine the sclera area.

Beneficially, the threshold value is determined statistically from the data of the facial image. From a technical perspective, whiteness is calculated from a candidate sclera area and a $90^{th}$ percentile value is calculated from the candidate sclera area. The threshold is the percentile value divided by a constant number (for example 1.3, wherein the constant number is empirically determined). Moreover, "whiteness" is a measure of brightness minus a red color content.

Optionally, the method comprises calculating a normalization factor from color values of the sclera area. More optionally, the method comprises normalizing colors of the facial image using the normalization factor. More optionally, the method comprises calculating an iris color value from color values of the iris area. More optionally, the method comprises calculating a pupil color value from color values of the pupil area.

Optionally, the method comprises determining an eye color of the user from the color values of the sclera area, the iris color value and the pupil color value. Sclera color is only used to correct an estimated color bias. Thus, if the sclera appears to be red, redness is reduced until the sclera looks white. Pupil color has no influence. Iris color is a main source for estimation. The iris area is masked for the best location and the image is converted, for example, into "lab color space". Mean lab color coordinates from the mask area give three parameters that are segmented into eye color classes based on a decision tree. It will be appreciated that a decision tree is a logical list of rules that operates on the input values and guides a process into branches depending on the values.

Optionally, the method comprises determining a skin tone of the user using color values of the facial image.

According to a second aspect, there is provided a system for finding at least one area of interest of a graphical representation of an eye from a facial image, the system comprising a memory configured to store instructions; a data processing arrangement that is configured to execute the instructions to
   receive the facial image of a user as an input data;
   detect a first area from the facial image, wherein the first area comprises the graphical representation of the eye of the user and the first area is surrounded by an edge;
   determine a center point of an iris and a radius of the iris of the graphical representation of the eye by scanning the first area using at least one directional filter.

Optionally, in the system, the data processing arrangement is further configured to execute the instructions to determine a sclera area of the graphical representation of the eye to be an area between the edge and a circle, the circle having the determined center point of the iris and the radius of the iris.

Optionally, in the system, the data processing arrangement is further configured to determine a pupil area of the graphical representation of the eye by implementing a contrast analysis and the center point of the iris and the radius of the iris.

Optionally, in the system, the data processing arrangement is configured to determine an iris area to be an area between the circle having the center point and the radius of the iris and the pupil area.

According to a third aspect, there is provided a computer program comprising computer readable instructions adapted to perform the method according to the embodiments of the present disclosure.

According to the embodiments, the system is implemented using the image capturing device that is communicatively connected to the at least one input interface through a network. The network is implemented as a wired network, a wireless network, or a combination of the wired network and the wireless network. Beneficially, the network is implemented using the Internet®. Beneficially, the image capturing device is a camera, a mobile phone, e-reader, PDA (Personal Digital Assistant), a tablet, a computer, an electronic notebook or a smartphone. For example, the system is implemented using a tablet computer, a desktop computer, a personal computer or an electronic notebook computer. Beneficially, the at least one input interface is communicatively connected to the data processing arrangement.

The eye segmentation system comprises at least one data storage medium that is coupled to the data processing arrangement, wherein the at least one data storage medium stores the facial image in the at least one data storage medium, for example in data memory.

The system beneficially employs a server that is coupled via a network in communication with the image capturing device. In operation, the server receives data of the facial image from the image capturing device and processes the data of the facial image to segment from the facial image a portion of the facial image corresponding to an eye for analysis. The server may be e.g. a tablet computer, a desktop computer, a personal computer, an electronic notebook computer or a cloud server. The server performs functions of the data processing arrangement to segment a portion of a captured facial image corresponding to an eye.

Beneficially, the present system is implemented as a portable computing device. The portable computing device comprises a camera for capturing a facial image of the user. The portable computing device optionally enables the user to capture a facial image of the user's face. Optionally, the portable computing device is optionally a smartphone, a web pad, or a laptop with a camera. The portable computing device communicates, for example, the facial image to the server via a communication network and the server is configured to process the data of the facial image to segment a portion of the facial image corresponding to an eye. Alternatively, the portable computing device is configured to do all or part of data processing required in a local manner.

As aforementioned, the facial image of the user is captured by any image capturing device. Alternatively, the facial image comprises a picture of a face of the user, for example derived from an historical photographic image. The system is beneficially configured to process facial image data that is in any feasible format for image analysis. The facial image data includes a portion of data corresponding to a left eye and a right eye; the left eye and the right eye each comprises a region of eye white (sclera), an iris and a pupil. Potentially, a color of the iris varies from person-to-person, for example, blue, green, brown, etc. Usually, a color of the pupil is black. A feasible format of the facial image data optionally includes JPEG (or JPG) format, PNG format, GIF format, TIFF format, PSD format, PDF format, EPS format or an AI-suitable format.

When in operation, the system performs data processing of the facial image data to determine a plurality of eye landmarks around the left eye and the right eye, wherein the data processing employs image analysis algorithms. For achieving improved efficiency of data processing, the plurality of eye landmarks is defined as a rectangular area around the left eye and the right eye.

When the system processes the facial image data, a center point (x1, y1) of the eye is determined using the at least one directional filter. Conveniently, the directional filter is an edge detector that is used to compute first derivatives of the facial image. The first derivatives (or slopes) are most evident when a large change occurs between adjacent pixel values. The directional filters are optionally designed to filter for any direction within a given facial image. For images, x- and y-directional filters are commonly used to compute derivatives in their respective directions. As aforementioned, the center point of the eye is a center point of the pupil. As aforementioned, the center point of the pupil is determined using the at least one directional filter.

Beneficially, the present system employs a Bayesian analysis method which uses a pre-defined probability distribution to determine a center point of the eye and a radius of the pupil. In the Bayesian analysis method, the center point of the eye is determined by identifying a point that is closer to the center of the eye area than to the borders and is represented mathematically. Beneficially, the radius of the iris is determined by combining the pre-defined probability distribution with a measurement of the radius of the iris to obtain a posterior probability distribution. From the posterior probability distribution, a highest radius value of the iris is determined as the radius of the iris. Optionally, the radius of the pupil is determined as a combination of a radial scan of an image brightness change and the pre-defined probability distribution. Optionally, a spatially abrupt image brightness change is indicative of a pupil border.

From the radius of the iris, the present system defines a sclera area, using the rectangular area defined by the at least one eye landmark, by extracting the pupil from the facial image. Optionally, the sclera color is measured by analyzing the defined sclera area using an average value of that area. Optionally, a sclera criteria is defined as being (a) bright relative to an aggregated brightness of the facial image, or (b) low color ("no color", namely relatively indistinguished in color from an aggregate color of the facial image). Optionally, the sclera criteria is calculated for the rectangular area, after which a statistically estimated threshold value from the sclera criteria is applied to select a "best sclera area".

Beneficially, the data processing arrangement of the system determines a plurality of eye landmarks around the left eye and the right eye using an image processing technique. Beneficially, the image processing technique is a digital image processing technique, for example as aforementioned.

Optionally, the plurality of the eye landmarks is detected using a facial landmark detection technique. The facial landmark detection technique is susceptible to being implemented using a machine learning model to identify frontal human faces in the facial image and estimate their pose with the plurality of eye landmarks on the face of the user. The machine learning model is beneficially implemented as a recursive neural network that can learn by experience regarding how to perform eye segmentation on a series of teaching facial images. Optionally, the facial landmark detection technique comprises at least one of the Histogram of Ordered Gradients (HOG) feature combining with a linear classifier algorithm, an image pyramid technique, or a sliding window detection technique. The facial landmark detection technique optionally predicts a position of the plurality of eye landmarks on the facial image of the user including points on an eyelid and canthi. Beneficially, the facial landmark detection technique is applied to detect points of interest on the facial image using machine learning models, as aforementioned. In an embodiment, the plurality of eye landmarks near the eyebrows are used to extract the eye regions from the facial image.

The data processing arrangement is beneficially configured to apply the at least one directional filter in at least two directions separately to scan over an area of the eye to determine the center point of the eye and the radius of the iris. Optionally, the at least two directions are mutually orthogonal. The at least one directional filter scans the eye area separately in x and y directions. Optionally, the at least one directional filter has one or more parameters that may be fully scanned. The one or more parameters optionally include at least one of: a x-axis, a y-axis, the radius (r) of the iris. Beneficially, the x-axis, y-axis, and the radius (r) of the iris all have a minimum value or a maximum value. Beneficially, the at least one directional filter scans through loops of all combinations of the one or more parameters.

Beneficially, at least one quality metric is balanced based on a combination of at least a first metric, and a second metric, to determine the eye that is suitable for segmentation, wherein the first metric and the second metric are selected from an eye openness, an eye area image brightness or an eye area image overexposure.

An eye area is beneficially defined as a portion of a facial image that is spatially close around the eye including the eye and surroundings of the eye. A problem arises when an image overexposure potentially arises due to light illuminating excessively the facial image (saturated pixels with close to maximum brightness). When the system is in operation, a selection is made: (i) when the left eye is more open than the right eye, the left eye is selected to be suitable for segmentation, (ii) when the right eye area is brighter than the left eye (i.e. the left eye is in a shadow), the right eye is selected to be suitable for segmentation, and (iii) when the right eye area has image overexposure compared to the left eye, the left eye is selected to be suitable for segmentation.

Beneficially, the plurality of eye landmarks is defined as a rectangular area around each of the left eye and the right eye, wherein the rectangular area comprises about 4 to 8 eye landmarks around each of the left eye and the right eye. Optionally, a number of eye landmarks around the left eye and the right eye are 6, for example. Optionally, the number of eye landmarks around the left eye and the right eye are in a range of 4 or 8.

When the system is in operation, the image analysis determines an eye (i.e. a left eye or a right eye) from the facial image which is suitable for eye segmentation. For example, if the right eye is fully open and the left eye is partly closed, a first rectangular area defined by the left eye is smaller than a second rectangular area defined by the right eye. In such a case, the second rectangular area defined by the right eye is selected for eye segmentation. Based on the second rectangular area defined by the right eye, the right eye is selected as a suitable eye for the eye segmentation. When the iris is blocked by eyelids in the facial image, a part of the circular iris area that is within the rectangular area is selected for eye segmentation.

When the system is in operation, the data processing arrangement
  (a) determines a range of values for at least one of the center point of the eye or the radius of the iris or pupil by scanning an area of the eye using the at least one directional filter in multiple mutually different directions;
  (b) determines the values for at least one of the center point of the eye or the radius of the iris or pupil based on an angle or a shape of the at least one directional filter; and
  (c) determines a suitable value for at least one of the center point of the eye or the radius of the iris or pupil by analyzing the range of values for at least one of the center point of the eye or the radius of the iris or pupil.

Optionally, at least one of a range of values for center points (e.g. x-axis, y-axis), and the radius (r) of the iris are determined using the at least one directional filter. The ranges for x-axis include x1, x2, x3, . . . xn, the ranges for y-axis includes y1, y2, y3, . . . yn, and the ranges for the radius (r) of the iris include r1, r2, r3, . . . rn. Beneficially, an angle or a shape of the at least one directional filter is included as one of the parameters of the at least one directional filter.

When using directional filtering in the system, the at least one directional filter starts to scan a range of values for x-axis, y-axis, for example to compute the radius (r) of the iris, based on pre-defined parameters or settings being used for configuring the at least one directional filter. The parameters of the at least one directional filter are beneficially adjusted according to a rule, for example an updated rule, until a stop condition is reached. A best match that includes at least one of: (i) values for x-axis, y-axis; (ii) the radius (r) of the iris; this best match is identified from the scans of the at least one directional filter. The best match is, for example, a best correlation, a best score or a best probability.

When the system is in operation, the data processing arrangement determines a sclera area, using the rectangular area defined by the at least one eye landmark, by extracting the pupil from the facial image data, wherein the data processing arrangement determines the sclera area by calculating and combining at least one sclera criteria for the rectangular area, and by applying a statistically estimated threshold value from the at least one sclera criteria. In an embodiment, the sclera color is beneficially measured by analyzing the defined sclera area using an average value of that area. In an embodiment, a sclera criterion is defined as being (a) bright, or (b) having a low color content ("no color", for example grey with a low color contrast to other portions of the facial image). Beneficially, the threshold value is dynamically varied, based on an aggregated content of the facial image data, wherein the threshold value is beneficially adaptively changed when processing a series of facial image; in other words, in the system, the threshold value is beneficially not constant in value. For example, the present system uses a median estimator to determine the sclera area. Alternatively, the present system uses an average estimator to determine the sclera area.

Beneficially, the system for finding at least one area of interest of a graphical representation of an eye from a facial image is configured to determine the radius of the iris by determining a first radius of the iris by sliding a first directional filter over an area of the eye in a predetermined way; determining a second radius of the iris by sliding a second directional filter over the area of the eye in a predetermined way; and determining the radius of the iris, from the first radius or the second radius of the iris, that is correlated with the center point of the eye.

Beneficially, the first directional filter is a circular directional filter. The first directional filter determines a first radius (r1) of the iris. The first directional filter is scanned or slid over an area of the eye in a first predetermined manner to determine the first radius of the iris. The first predetermined manner includes, for example, sliding systematically all x values, and then indexing y values, etc. The area of scan within the image of the facial image is beneficially determined using the plurality of eye landmarks.

Beneficially, when the system is in operation, the second directional filter determines a second radius (r2) of the iris. The second directional filter is scanned or slid over the eye area in the first predetermined manner. Optionally, the second directional filter is scanned or slid over the area of the eye in a second predetermined manner, which is different from the first predetermined manner. Optionally, the second radius (r2) of the iris is different from the first radius (r1) of the iris. Optionally, a range of radii of the iris is determined in the above similar way using the circular directional filter, and then a best correlation with circular form of the iris provides a measure of the center point (x1, y1) of the eye.

Optionally, the aforesaid at least one directional filter processes data of a region that is oval in shape, wherein the at least one directional filter that is oval in shape is slid over the area of the eye in a predetermined manner for determining the radius of the iris.

The at least one directional filter that is oval in shape optionally has different diameters in one direction than another direction. The at least one directional filter that is oval in shape is slid, for example, in the same predetermined manner as used for the circular directional filter. The at least one directional filter that is oval in shape is optionally rotated for different slidings and a best correlation of values enables the center point (x1, y1) of the eye to be computed. In a case of the oval shaped directional filter, the radius and a rotational angle of the oval shaped directional filter is used as an initial value for the radius of the iris or pupil. However, it will be appreciated that the radius of pupil potentially changes as a function of illumination conditions when the facial image is captured. From the radius of pupil and the radius of the iris, an area which defines the iris is determined, which in turn is used to determine a color of the iris in an efficient way.

Optionally, when the system is in operation, the system is configured to perform a Bayesian analysis to: formulate a prior probability distribution to determine the center point of the eye and the radius of the iris; identify a point that is closer to a center of an eye area to determine the center point of the eye; combine the prior probability distribution with a measurement of the radius of the iris to obtain a posterior probability distribution; and determine the radius of the iris by identifying a radius of the iris that has a maximum value from the posterior probability distribution.

Beneficially, when the system is in operation, the radius of the iris is determined as a combination of a radial scan of image brightness change using the at least one directional filter and the prior probability distribution.

The system beneficially uses a method of segmenting a portion of facial image data corresponding to an eye to determine a center point of the eye, a radius of an iris of the eye, and an area of interest of the eye from a white area of the eye, wherein the method comprises receiving, when in operation, a facial image of a user from an image capturing device; determining an eye that is suitable for segmentation from a left eye and a right eye using at least one quality metric; determining a center point of the eye using at least one directional filter; determining, using the at least one directional filter, a radius of an iris of the eye from the center point of the eye; using a contrast analysis to determine a pupil of the eye using the center point of the eye and the radius of the iris; determining a white area of the eye by removing the iris of the eye; and determining an area of interest from the white area by normalizing the white area using white normalization.

Beneficially, the method comprises determining a plurality of eye landmarks around the left eye and the right eye using an image processing technique. Beneficially, the method comprises applying the at least one directional filter in at least two directions separately to scan over an area of the eye to determine the center point of the eye and the radius of the iris.

The advantages of the present system, and an associated computer program product executed in data processing hardware of the system, are thus disclosed above, wherein stochastic artefacts in the facial image have less influence when analysing the portion of data of the facial image data corresponding to one or more eyes. Filtering of such stochastic artefacts effectively enables the system to perform noise reduction; noise reduction is signals is conventionally regarded as being a technical effect.

Embodiments of the present disclosure automate the segmentation process by segmenting a portion of data corresponding to the eye from captured facial image data of the user, even when the user uses eyeglasses or the user's eye is partly closed in the facial image, or the facial image of the user is of a low quality; "low" includes, for example low spatial resolution, low color contrast, blurred facial image, and so forth. Embodiments of the present disclosure optionally reduce the effect of artificial edges created on the facial image due to random noise using directional filtering, thereby improving the detection of the eye and its parts more accurately. Embodiments of the present disclosure optionally reduce the false matches with perfect data. Embodiments of the present disclosure optionally scan the facial image data in several mutually-different directions to determine an exact center point of the eye and the radius of the iris. Embodiments of the present disclosure optionally determine a color of the eye in a more accurate and efficient way to provide recommendations on one or more cosmetic products to the user.

Detailed Description of the Drawings

Figure 1:
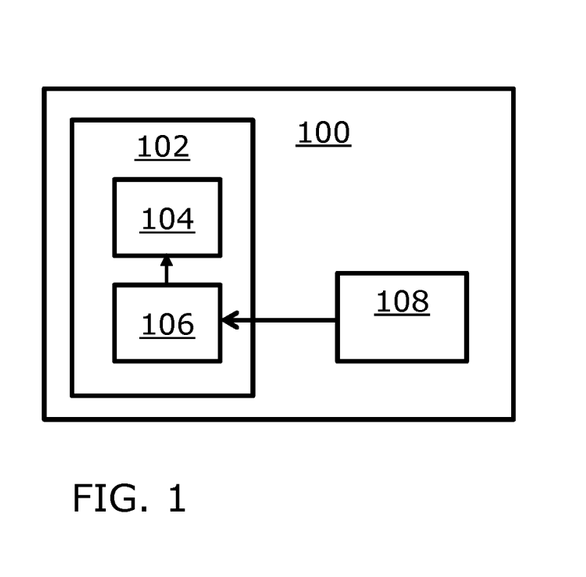
FIG. 1 is a schematic illustration of a system according to an embodiment of the present disclosure.

FIG. 1 is a schematic illustration of a system 100 in accordance with an embodiment of the present disclosure. The system 100 comprises an eye segmentation system 102 that comprises a data processing arrangement 104 and at least one input interface 106. When in operation, the at least one input interface 106 receives a facial image of a user from an image capturing device 108 and generates corresponding facial image data. The data processing arrangement 104 receives, when in operation, the facial image data of the user as an input data and processes the input data to segment a portion of the input data corresponding to an eye to determine a center point of the eye, a radius of an iris of the eye, and an area of interest from a white area (i.e. sclera) of the eye. In an embodiment, the at least one input interface 106 is communicatively connected to the data processing arrangement 104. In an embodiment, the at least one input interface 106 is communicatively connected to the data processing arrangement 104 through a network. The functions of these parts are as described above.

Figure 2:
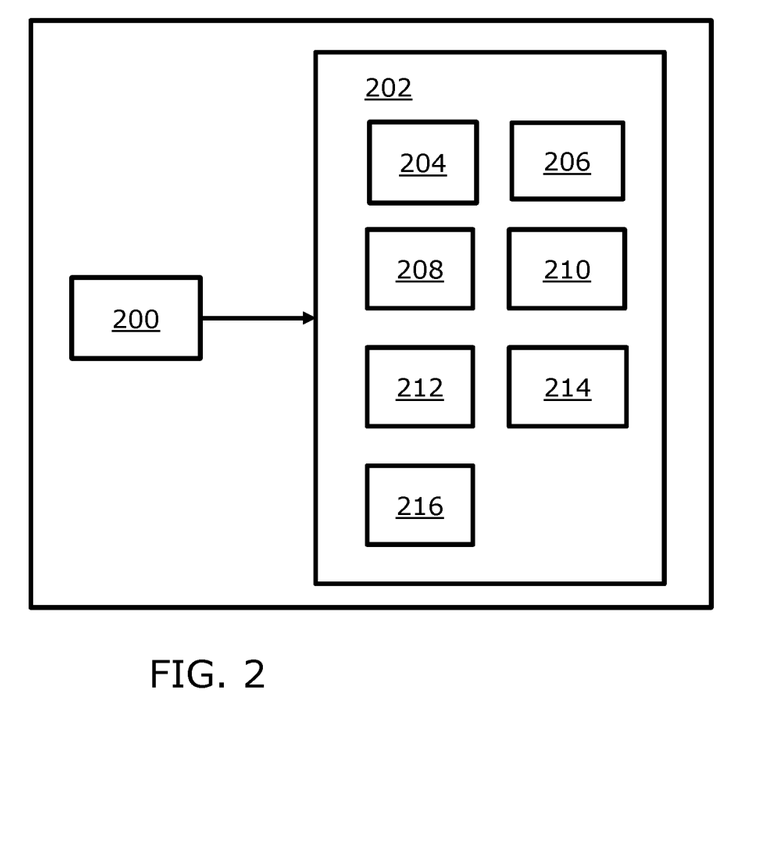
FIG. 2 is a functional block diagram of a system according to an embodiment of the present disclosure.

Referring next to FIG. 2, there is shown an illustration of a functional block diagram representing a system in accordance with an embodiment of the present disclosure. The functional block diagram of the system comprises at least one input interface 200 and a data processing arrangement 202. The functions of these parts are as described above. The data processing arrangement 202 includes a facial image receiving module 204, a suitable eye determination module 206, an eye center point determination module 208, an iris radius determination module 210, a pupil determination module 212, a sclera determination module 214 and an area of interest determination module 216. These modules are beneficial implemented in hardware units (for example implemented using FPGA's), as software executable on computing hardware, or a combination thereof. The facial image receiving module 204 receives the facial image of the user as input data and processes the input data to segment a portion of the input data corresponding to an eye. The suitable eye determination module 206 determines an eye that is suitable for segmentation from a left eye and a right eye using at least one quality metric. The eye center point determination module 208 determines a center point of the eye using at least one directional filter. The iris radius determination module 210 determines a radius of an iris of the eye from the center point of the eye using the at least one directional filter. The pupil determination module 212 determines a pupil of the eye using the center point of the eye and the radius of the iris, using a contrast analysis. The sclera determination module 214 determines a white area by removing the iris of the eye. The area of interest determination module 216 determines an area of interest from the white area by normalizing the white area using white normalization.

Figure 3:
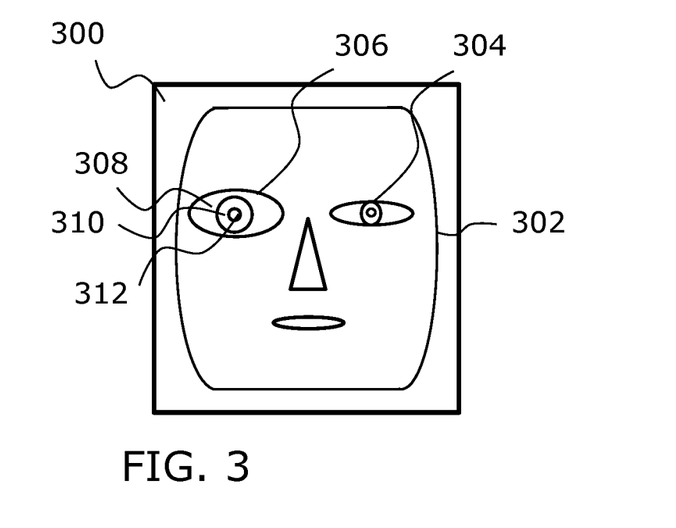
FIG. 3 is an illustration of an example facial image captured by an image capturing device according to an embodiment of the present disclosure.

In FIG. 3, there is shown an illustration of an example facial image 300 captured by an image capturing device in accordance with an embodiment of the present disclosure. The facial image 300 includes a graphical representation of a face 302 comprising a graphical representation of a left eye 304 and a right eye 306, both including a sclera 308, an iris 310 and a pupil 312.

Figure 4:
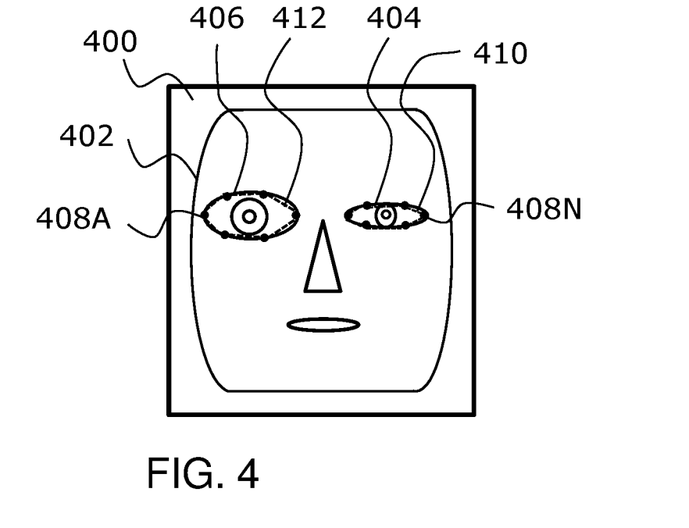
FIG. 4 is an illustration of an example facial image after an initial level of image analysis is performed by a system according to an embodiment of the present disclosure.

In FIG. 4, there is shown an illustration of an example facial image 400 after an initial level of image analysis performed by a system in accordance with an embodiment of the present disclosure. The facial image 400 includes a picture of a face 402. The face 402 includes a left eye 404 and a right eye 406. Both the left eye 404 and the right eye 406 includes a plurality of eye landmarks 408A-408N. The plurality of eye landmarks 408A-408N is defined as a first rectangular area 410 around the left eye 404 and as a second rectangular area 412 around the right eye 406. In an embodiment, the plurality of eye landmarks 408A-408N around the left eye 404 and the right eye 406 are determined using the initial level image analysis. In an embodiment, a number of eye landmarks 408A-408N around the left eye 404 and the right eye 406 is six (6). In another embodiment, the number of eye landmarks 408A-408N around the left eye 404 and the right eye 406 are four (4) or eight (8). In an embodiment, the initial level image analysis determines an eye which is better for eye segmentation. In an embodiment, for example, if the right eye 406 is fully open and the left eye 404 is partly closed, the first rectangular area 410 defined by the left eye 404 is smaller than the second rectangular area 412 defined by the right eye 406. In this case, the second rectangular area 412 defined by the right eye 406 is selected to be suitable for the eye segmentation.

Figure 5:
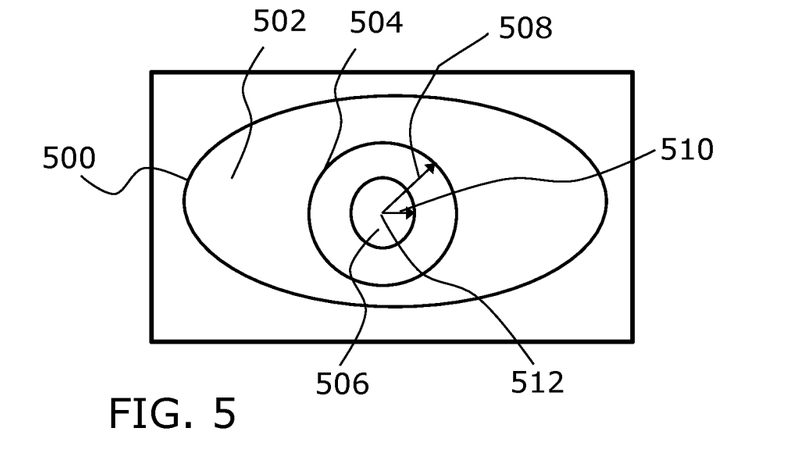
FIG. 5 is an illustration of an eye of a facial image comprising a sclera, an iris and a pupil according to an embodiment of the present disclosure.

In FIG. 5, there is shown an illustration of an eye 500 of a facial image comprising a sclera 502, an iris 504 and a pupil 506 in accordance with an embodiment of the present disclosure. The eye 500 includes the sclera 502, the iris 504 and the pupil 506. In an embodiment, the present system determines a radius of the iris 508, a radius of the pupil 510 and a center point 512 of the eye 500 as described above.

Figure 6A:
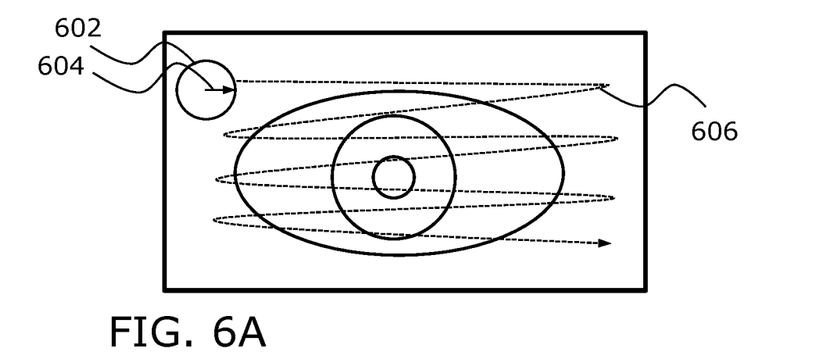
FIGS. 6A-6B are illustrative examples of at least one directional filter that is used by a system according to an embodiment of the present disclosure.
Figure 6B:
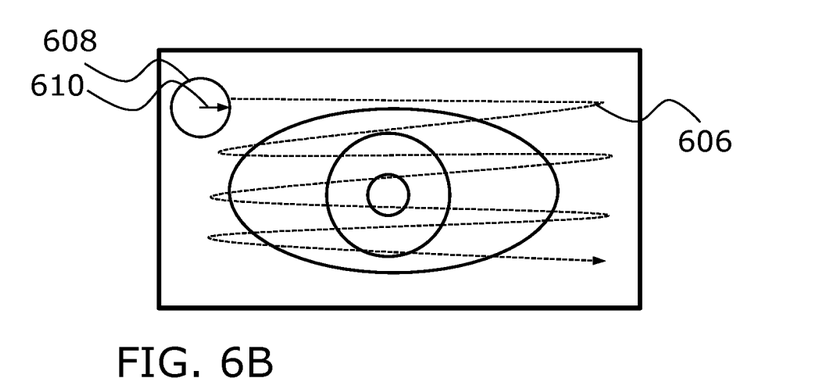

Referring next to FIGS. 6A-6B, there are shown illustrative examples of at least one directional filter that is used by a system in accordance with an embodiment of the present disclosure. The at least one directional filter includes a first directional filter 602 that determines a first radius (r1) of the iris 604 from a facial image of a user. The first directional filter 602 is slid over an eye area through a first predetermined way 606. The first predetermined way 606, for example, includes sliding systematically all x values, then indexing y values etc. The area of scan within the facial image is beneficially determined using a plurality of eye landmarks determined by an initial image analysis. The at least one directional filter includes a second directional filter 608 that determines a second radius (r2) of the iris 610. The second directional filter 608 is slid over the eye area through the first predetermined way 606. The second radius (r2) of the iris 610 is optionally different from the first radius (r1) of the iris 604. In the embodiment, for example, the center point (x1, y1) of the eye is determined using the at least one directional filter (602, 608). The at least one directional filter (602, 608) is beneficially oval in shape and is slid over the area of the eye in a predetermined way for determining the radius of the iris of the eye. The at least one directional filter (602, 608) that is oval in shape optionally has different diameters in one direction than another direction. The at least one directional filter (602, 608) that is oval in shape is slid in a same way like employed for the circular directional filter. The at least one directional filter (602, 608) that is oval in shape is beneficially rotated for different slidings and the best correlation with circular form of the iris is used to compute the center point (x1, y1) of the eye. In the embodiment, in a case of the directional filter (602, 608) that is oval in shape, the radius and a rotational angle of the directional filter (602, 608) that is oval in shape is used as an initial value for the radius of the iris or pupil. Sometimes, the radius of pupil potentially changes based on illumination conditions. In the embodiment, the at least one directional filter (602, 608) scans an eye area separately in x and y directions. The at least one directional filter (602, 608) has one or more parameters that may be fully scanned. The one or more parameters optionally include x-axis, y-axis, and the radius of the iris r. In the embodiment, the x-axis, y-axis, and the radius r all have a minimum value and a maximum value. In the embodiment, the at least one directional filter (602, 608) scan through the loops of all combinations of the one or more parameters.

Figure 7A:
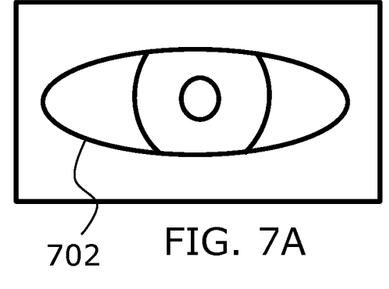
FIGS. 7A-7F are illustrations of an example of a basic filter versus at least one directional filter used in segmenting an eye which is partly closed according to an embodiment of the present disclosure.
Figure 7B:
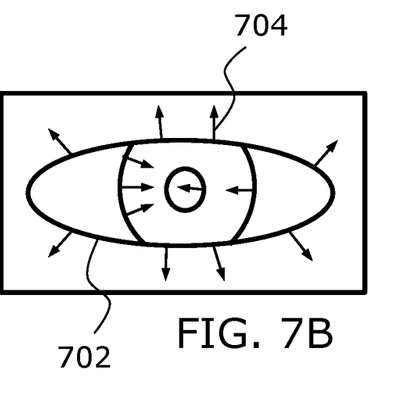
Figure 7C:
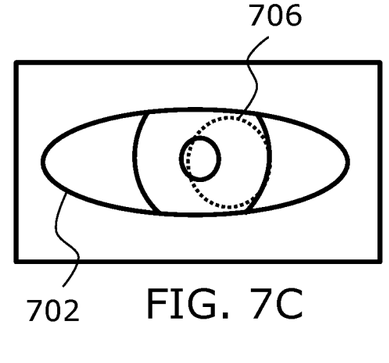
Figure 7D:
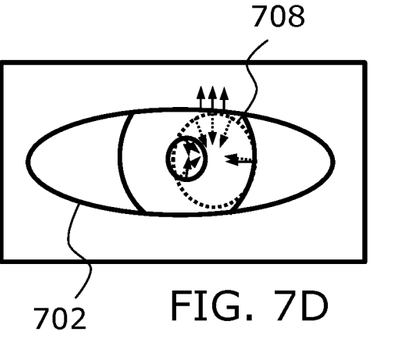
Figure 7E:
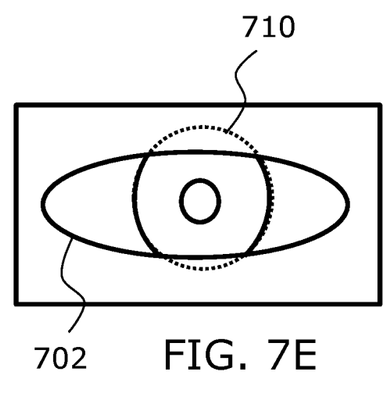
Figure 7F:
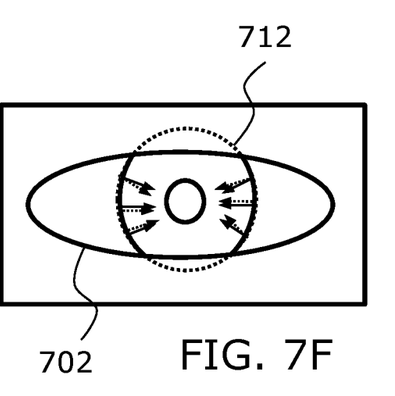

In FIGS. 7A-7F, there are shown illustrations of an example of a basic filter versus at least one directional filter used in segmenting an eye which is partly closed in accordance with an embodiment of the present disclosure. FIGS. 7A through 7F each include an image of an eye 702. In the embodiment, image edges are detected using the basic filter as depicted in FIG. 7A. The image edges with directions 704 are detected using the at least one directional filter of the present system as depicted in FIG. 7B. In one example, the basic filter 706, as shown in FIG. 7C, is relatively well covered by edge areas and a strong match of the basic filter 706 is depicted in FIG. 7C. The at least one directional filter 708 being circular in shape of FIG. 7D depicts the edge directions 704, and many directions are wrong and the match is weaker as depicted in FIG. 7D for the same image of the eye 702. In another example, a relatively weak match 710 of the basic filter is depicted in FIG. 7E. A relatively strong match 712 of the at least one directional filter is depicted in FIG. 7F. The present system processes reliably, despite stochastic noise being present, very low-quality images that are captured in poor illumination conditions. The system reduces an effect of artificial edges created on the facial image due to random noise using directional filtering, thereby improving the detection of the eye and its parts more accurately. In the embodiment, the present system reduces false matches with perfect data. In the embodiment, the present system scans in several directions to determine an exact center point of the eye 702 and a radius of the eye 702.

Figure 8:
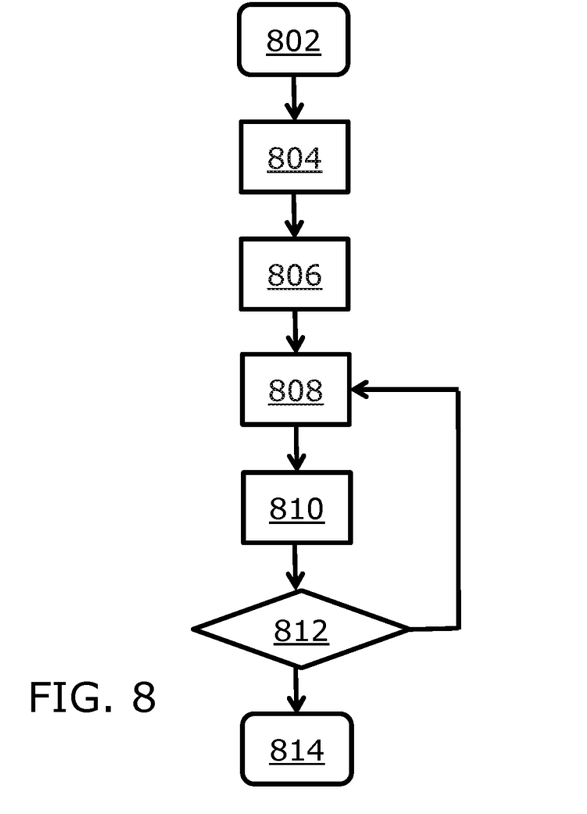
FIG. 8 is an illustration a process flow for applying at least one directional filter based on the parameters x, y, and r according to an embodiment of the present disclosure.

Referring next to FIG. 8, there is shown an illustration of a process flow for applying at least one directional filter based on the parameters x, y, and r in accordance with an embodiment of the present disclosure. At a step 802, the at least one directional filter is started. At a step 804, a center point (x1, y1) of the eye is determined and set n=1, where n is a number of iterations of the at least one directional filter to scan through an eye area to determine a continuous range of values for x, y, and r. The ranges of x include x1, x2, x3, . . . xn, the ranges of y include y1, y2, y3, . . . yn and the ranges of r include r1, r2, r3, . . . rn. An angle or a shape of the at least one directional filter is optionally included as one of the parameters of the at least one directional filter. At a step 806, an initial value at point (xn, y1) is set. At a step 808, the eye area is scanned through the ranges by starting from the best prior parameters and by adjusting them until a stop condition is reached. A best match that includes the values for x-axis, y-axis, and/or the radius (r) of the iris is identified from the scans of the at least one directional filter. The best match is beneficially a best correlation, a best score or a best probability. The above-mentioned steps are used to determine ranges of the radius of the iris and the radius of the pupil. At a step 810, a color value at point (xn, y1) is read. At a step 812, the radius of the eye is determined if the color value is greater than a threshold value. If the color value is not greater than the threshold value, the process flow continues to the step 808. At a step 814, the radius of the eye is determined.

Figure 9:
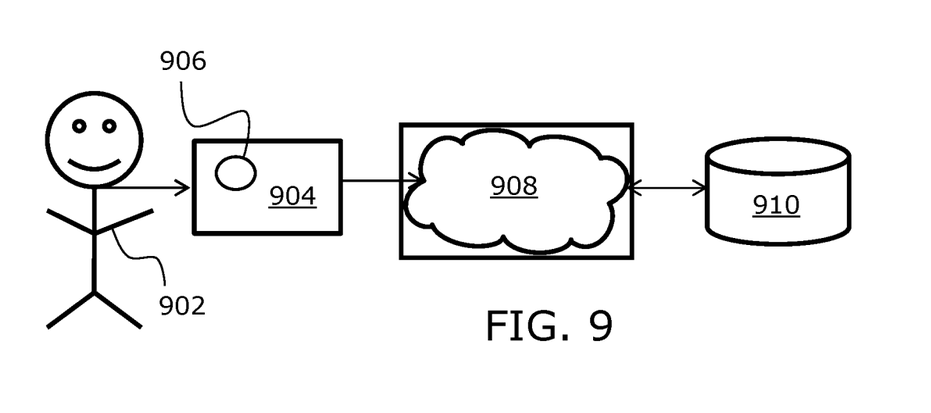
FIG. 9 is an illustration of an example view of a system, according to an embodiment of the present disclosure.

Referring next to FIG. 9, there is shown an illustration of an example view of a system, in accordance with an embodiment of the present disclosure. The system includes a portable computing device 904, a communication network 908 and a system server 910. The portable computing device 904 includes a camera 906. In the embodiment, the portable computing device 904 is used by a user 902 to capture a facial image of a face of the user 902. The portable computing device 904 is optionally a smartphone, a web pad, a laptop with a camera. The portable computing device 904 is configured to communicate the facial image of the user 902 over the communication network 908 to the server system 910. The server system 910 processes the facial image to segment an eye to determine a center point, a radius of an iris, and an area of interest from a white area of the eye. The server system 910 determines a center point of the eye and therefrom determines a white area of the eye. In an embodiment, the portable computing device 904 is configured to do all or part of the processing.

Figure 10:
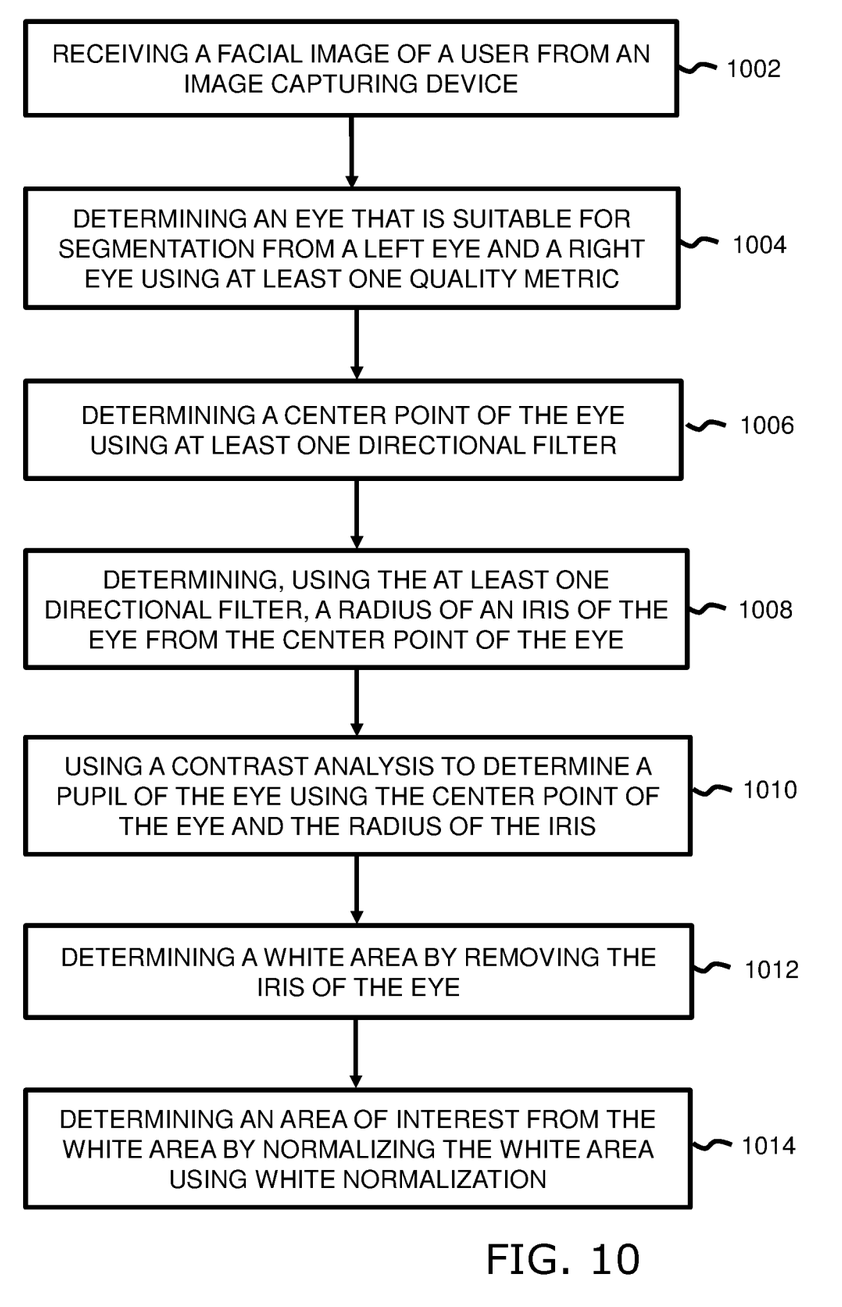
FIG. 10 is a flowchart, wherein the flowchart depicts steps of a method for finding at least one area of interest of a graphical representation of an eye from a facial image, according to an embodiment of the present disclosure.

Referring next to FIG. 10, there is shown an illustration of a flowchart illustrating steps of a method for finding at least one area of interest of a graphical representation of an eye from a facial image, in accordance with an embodiment of the present disclosure. At a step 1002, a facial image of a user from an image capturing device is received. At a step 1004, an eye that is suitable for segmentation, from a left eye and a right eye, is determined using at least one quality metric. At a step 1006, a center point of the eye is determined using at least one directional filter. At a step 1008, a radius of the iris of the eye from the center point of the eye is determined using the at least one directional filter. At a step 1010, using the center point of the eye and the radius of the iris, a pupil of the eye is determined using a contrast analysis. At a step 1012, the white area (sclera) is determined by removing the iris of the eye. At a step 1014, the area of interest is determined from the white area by normalizing the white area using white normalization.

Figure 11:
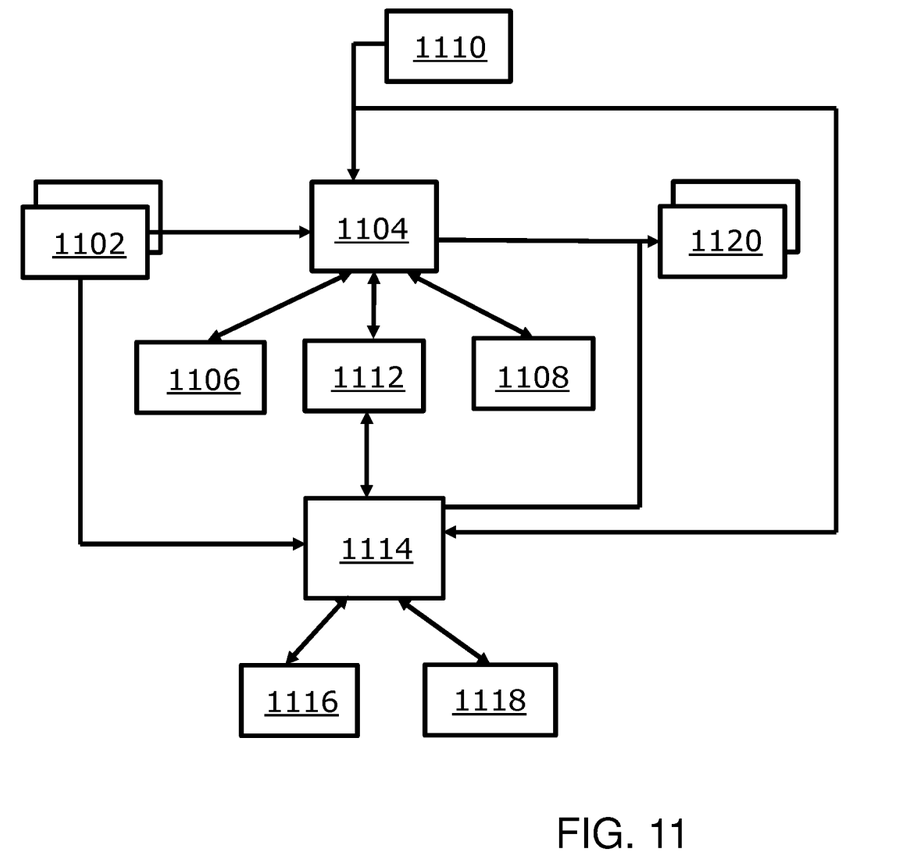
FIG. 11 is an illustration of an exploded view of a computing architecture according to an embodiment of the present disclosure.

In FIG. 11, there is shown an illustration of an exploded view of a system, including a computing architecture, in accordance with an embodiment of the present disclosure, wherein the system comprises at least one input interface 1102, a control module that comprises a data processing arrangement 1104, a memory 1106 and a non-volatile storage 1108, processing instructions 1110, storage 1112, and an image capturing device that comprises a processor 1114, a memory 1116 and a non-volatile storage 1118 and an output interface 1120. The functions of the data processing arrangement 1104, the least one input interface 1102 are as described above and cooperate together to implement methods of the disclosure as described in the foregoing.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for finding at least one area of interest of a graphical representation of an eye from a facial image, the method comprising a processor executing non-transitory machine readable instructions configured to implement the steps of:
   receiving the facial image of a user as an input data;
   detecting a first area from the facial image, wherein the first area comprises the graphical representation of the eye of the user and the first area is surrounded by an edge;
   determining a center point of an iris and a radius of the iris of the graphical representation of the eye by scanning the first area using at least one directional filter.

2. The method according to claim 1, wherein the method comprises determining a sclera area of the graphical representation of the eye to be an area between the edge and a circle, the circle having the determined center point of the iris and the radius of the iris.

3. The method according to claim 1, wherein the method further comprises determining a pupil area of the graphical representation of the eye by implementing a contrast analysis and using the center point of the iris and the radius of the iris.

4. The method according to claim 1, wherein the method further comprises determining an iris area to be an area between the circle having the center point and the radius of the iris and the pupil area.

5. The method according to claim 1, wherein the method further comprises determining the edge of the first area by identifying at least one eye point around the graphical representation of the eye using an image processing technique.

6. The method according to claim 1, wherein determining the center point of the iris comprises scanning, using the at least one directional filter, x values of the first area in a first direction and scanning, using the at least one directional filter, in a second direction to index y values of the first area.

7. The method according to claim 6, wherein determining the center point of the iris further comprises identifying a point that is correlating to a center of the first area based on the scanning the first area using the at least one directional filter in the first direction and the second direction.

8. The method according to claim 1, wherein determining the radius of the iris comprises
   determining a first radius of the iris by applying a first directional filter over the first area through a first path, wherein applying the first directional filter over the first area through the first path comprises (i) scanning, using the first directional filter, x values of the first area in a first direction, and (ii) scanning, using the first directional filter, the first area in a second direction to index y values of the first area;
   determining a second radius of the iris by applying a second directional filter over the first area through the first path, wherein applying the second directional filter over the first area through the first path comprises (i) scanning, using the second directional filter, x values of the first area in the first direction, and (ii) scanning, using the second directional filter, the first area in the second direction to index y values of the first area; and
   identifying the radius of the iris, from the first radius or the second radius of the iris, which is correlated with the center point of the iris.

9. The method according to claim 3, wherein the method comprises determining a radius of the pupil area by:
   performing a radial scan, using the at least one directional filter, over the graphical representation of the eye;
   identifying a brightness change in the first area to determine a border of the pupil area; and combining the identified brightness change of the graphical representation of the eye and probability distribution of the radius of the pupil area.

10. The method according to claim 1, wherein determining the sclera area comprises:
calculating a first sclera criteria and a second sclera criteria for the graphical representation of the eye;
combining the first sclera criteria and the second sclera criteria with the first area of the graphical representation of the eye to calculate a threshold value; and
applying the threshold value on the graphical representation of the eye to determine the sclera area.

11. The method according to claim 1, wherein the method comprises calculating a normalization factor from color values of the sclera area.

12. The method according to claim 11, wherein the method comprises normalizing colors of the facial image using the normalization factor.

13. The method according to claim 12, wherein the method comprises calculating an iris color value from color values of the iris area.

14. The method according to claim 12, wherein the method comprises calculating a pupil color value from color values of the pupil area.

15. The method according to claim 11, wherein the method comprises determining an eye color of the user from the color values of the sclera area, the iris color value and the pupil color value.

16. The method according to claim 12, wherein the method comprises determining a skin tone of the user using color values of the facial image.

17. A system for finding at least one area of interest of a graphical representation of an eye from a facial image, the system comprising a memory configured to store non-transitory machine readable instructions; a data processing arrangement that is configured to execute the instructions to cause a processor of the data processing arrangement to:
receive the facial image of a user as an input data;
detect a first area from the facial image, wherein the first area comprises the graphical representation of the eye of the user and the first area is surrounded by an edge; and
determine a center point of an iris and a radius of the iris of the graphical representation of the eye by scanning the first area using at least one directional filter.

18. The system according to claim 17, wherein the data processing arrangement is further configured to execute the instructions to determine a sclera area of the graphical representation of the eye to be an area between the edge and a circle, the circle having the determined center point of the iris and the radius of the iris.

19. The system according to claim 17, wherein the data processing arrangement is further configured to determine a pupil area of the graphical representation of the eye by implementing a contrast analysis and the center point of the iris and the radius of the iris.

20. The system according to claim 17, wherein the data processing arrangement is configured to determine an iris area to be an area between the circle having the center point and the radius of the iris and the pupil area.

21. A computer program comprising computer readable instructions configured to perform the method of claim 1 when executed on a data processing arrangement.

* * * * *